US007091049B2

(12) United States Patent
Boga et al.

(10) Patent No.: US 7,091,049 B2
(45) Date of Patent: Aug. 15, 2006

(54) ENHANCED DIFFRACTION-BASED BIOSENSOR DEVICES

(75) Inventors: Rameshbabu Boga, Roswell, GA (US); Chibueze Obinna Chidebelu-Eze, Atlanta, GA (US); Rosann M. Kaylor, Cumming, GA (US); Xuedong Song, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 762 days.

(21) Appl. No.: 10/180,219

(22) Filed: Jun. 26, 2002

(65) Prior Publication Data

US 2004/0002110 A1    Jan. 1, 2004

(51) Int. Cl.
 *G01N 33/543*    (2006.01)

(52) U.S. Cl. ............. 436/518; 422/82.05; 422/82.08; 422/82.11; 435/5; 435/6; 435/7.2; 435/7.21; 435/7.32; 435/7.34; 435/7.37; 435/287.2; 435/288.7; 435/808; 435/7.31; 436/164; 436/172; 436/513; 436/524; 436/525; 436/527; 436/531; 436/805; 436/815; 436/816; 436/817

(58) Field of Classification Search ............. None
See application file for complete search history.

(56) References Cited

U.S. PATENT DOCUMENTS

| 3,641,354 A | 2/1972 | De Ment |
| 4,011,009 A | 3/1977 | Lama et al. |
| 4,274,706 A | 6/1981 | Tangonan |
| 4,312,228 A | 1/1982 | Wohltjen |
| 4,330,175 A | 5/1982 | Fujii et al. |
| 4,363,874 A | 12/1982 | Greenquist |
| 4,399,686 A | 8/1983 | Kindlund et al. |
| 4,416,505 A | 11/1983 | Dickson |
| 4,442,204 A | 4/1984 | Greenquist et al. |
| 4,477,158 A | 10/1984 | Pollock et al. |
| 4,480,042 A | 10/1984 | Craig et al. |
| 4,528,260 A | 7/1985 | Kane |
| 4,534,356 A | 8/1985 | Papadakis |
| 4,537,861 A | 8/1985 | Elings et al. |
| 4,552,458 A | 11/1985 | Lowne |
| 4,561,286 A | 12/1985 | Sekler et al. |
| 4,562,157 A | 12/1985 | Lowe et al. |
| 4,587,213 A | 5/1986 | Malecki |
| 4,596,697 A | 6/1986 | Ballato |
| 4,614,723 A | 9/1986 | Schmidt et al. |
| 4,632,559 A | 12/1986 | Brunsting |

(Continued)

FOREIGN PATENT DOCUMENTS

EP    0205698 A1    12/1986

(Continued)

OTHER PUBLICATIONS

Abstract of Japanese Patent No. JP2085755 Mar. 27, 1990.

(Continued)

*Primary Examiner*—Christopher L. Chin
(74) *Attorney, Agent, or Firm*—Dority & Manning, P.A.

(57) ABSTRACT

An enhanced diffraction based biosensor system and method are provided for detecting an analyte of interest in a test medium. The system incorporates at least one additional detection tag substance with the analyte of interest, the tag emitting a measurable parameter that is different from optical diffraction characteristics of the analyte. The biosensor may be a "fluoroptical" system wherein the detection tag is a fluorescence emitting substance, including fluorescent-labeled diffraction enhancing elements. The enhanced diffraction biosensor system may determine the presence of analytes in biological fluids both qualitatively and quantitatively.

21 Claims, 3 Drawing Sheets

U.S. PATENT DOCUMENTS

| | | |
|---|---|---|
| 4,647,544 A | 3/1987 | Nicoli et al. |
| 4,661,235 A | 4/1987 | Krull et al. |
| 4,690,715 A | 9/1987 | Allara et al. |
| 4,698,262 A | 10/1987 | Schwartz et al. |
| 4,776,944 A | 10/1988 | Janata et al. |
| 4,812,221 A | 3/1989 | Madou et al. |
| 4,815,843 A | 3/1989 | Tiefenthaler et al. |
| 4,818,710 A | 4/1989 | Sutherland et al. |
| 4,837,715 A | 6/1989 | Ungpiyakul et al. |
| 4,842,633 A | 6/1989 | Kuribayashi et al. |
| 4,842,783 A | 6/1989 | Blaylock |
| 4,844,613 A | 7/1989 | Batchelder et al. |
| 4,851,816 A | 7/1989 | Macias et al. |
| 4,876,208 A | 10/1989 | Gustafson et al. |
| 4,877,747 A | 10/1989 | Stewart |
| 4,882,288 A * | 11/1989 | North et al. ............... 436/525 |
| 4,895,017 A | 1/1990 | Pyke et al. |
| 4,917,503 A | 4/1990 | Bhattacharjee |
| 4,931,384 A | 6/1990 | Layton et al. |
| 4,992,385 A | 2/1991 | Godfrey |
| 4,999,489 A | 3/1991 | Huggins |
| RE33,581 E | 4/1991 | Nicoli et al. |
| 5,023,053 A | 6/1991 | Finlan |
| 5,035,863 A | 7/1991 | Finlan et al. |
| 5,055,265 A | 10/1991 | Finlan |
| 5,057,560 A | 10/1991 | Mueller |
| 5,063,081 A | 11/1991 | Cozzette et al. |
| 5,064,619 A | 11/1991 | Finlan |
| 5,071,248 A | 12/1991 | Tiefenthaler et al. |
| 5,076,094 A | 12/1991 | Frye et al. |
| 5,089,387 A | 2/1992 | Tsay et al. |
| 5,096,671 A | 3/1992 | Kane et al. |
| 5,114,676 A | 5/1992 | Leiner et al. |
| 5,124,254 A | 6/1992 | Hewlins et al. |
| 5,134,057 A | 7/1992 | Kuypers et al. |
| 5,137,609 A | 8/1992 | Manian et al. |
| 5,143,854 A | 9/1992 | Pirrung et al. |
| 5,152,758 A | 10/1992 | Kaetsu et al. |
| 5,155,791 A | 10/1992 | Hsiung |
| 5,182,135 A | 1/1993 | Giesecke et al. |
| 5,189,902 A | 3/1993 | Groeninger |
| 5,196,350 A | 3/1993 | Backman et al. |
| 5,225,935 A | 7/1993 | Watanabe et al. |
| 5,235,238 A | 8/1993 | Nomura et al. |
| 5,238,815 A | 8/1993 | Higo et al. |
| 5,242,828 A | 9/1993 | Bergstrom et al. |
| 5,262,299 A | 11/1993 | Evangelista et al. |
| 5,268,306 A | 12/1993 | Berger et al. |
| 5,280,548 A | 1/1994 | Atwater et al. |
| 5,304,293 A | 4/1994 | Tierney et al. |
| 5,310,686 A | 5/1994 | Sawyers et al. |
| 5,315,436 A | 5/1994 | Lowenhar et al. |
| 5,321,492 A | 6/1994 | Detwiler et al. |
| 5,327,225 A | 7/1994 | Bender et al. |
| 5,334,303 A | 8/1994 | Muramatsu et al. |
| 5,352,582 A | 10/1994 | Lichtenwalter et al. |
| 5,369,717 A | 11/1994 | Attridge |
| 5,374,563 A | 12/1994 | Maule |
| 5,376,255 A | 12/1994 | Gumbrecht et al. |
| 5,378,638 A | 1/1995 | Deeg et al. |
| 5,389,534 A | 2/1995 | von Gentzkow et al. |
| 5,402,075 A | 3/1995 | Lu et al. |
| 5,404,756 A | 4/1995 | Briggs et al. |
| 5,415,842 A | 5/1995 | Maule |
| 5,418,136 A | 5/1995 | Miller et al. |
| 5,424,220 A | 6/1995 | Goerlach-Graw et al. |
| 5,430,815 A | 7/1995 | Shen et al. |
| 5,436,161 A | 7/1995 | Bergstrom et al. |
| 5,451,683 A | 9/1995 | Barrett et al. |
| 5,455,178 A | 10/1995 | Fattinger |
| 5,455,475 A | 10/1995 | Josse et al. |
| 5,464,741 A | 11/1995 | Hendrix |
| 5,468,606 A | 11/1995 | Bogart et al. |
| 5,478,527 A | 12/1995 | Gustafson et al. |
| 5,482,830 A | 1/1996 | Bogart et al. |
| 5,482,867 A | 1/1996 | Barrett et al. |
| 5,489,678 A | 2/1996 | Fodor et al. |
| 5,489,988 A | 2/1996 | Ackley et al. |
| 5,492,840 A | 2/1996 | Malmqvist et al. |
| 5,496,701 A | 3/1996 | Pollard-Knight |
| 5,510,481 A | 4/1996 | Bednarski et al. |
| 5,510,628 A | 4/1996 | Georger, Jr. et al. |
| 5,512,131 A | 4/1996 | Kumar et al. |
| 5,514,501 A | 5/1996 | Tarlov |
| 5,514,559 A | 5/1996 | Markert-Hahn et al. |
| 5,516,635 A | 5/1996 | Ekins et al. |
| 5,518,689 A | 5/1996 | Dosmann et al. |
| 5,527,711 A | 6/1996 | Tom-Moy et al. |
| 5,552,272 A | 9/1996 | Bogart |
| 5,554,541 A | 9/1996 | Malmqvist et al. |
| 5,569,608 A | 10/1996 | Sommer |
| 5,573,909 A | 11/1996 | Singer et al. |
| 5,580,697 A | 12/1996 | Keana et al. |
| 5,580,921 A | 12/1996 | Stepp et al. |
| 5,585,279 A | 12/1996 | Davidson |
| 5,589,401 A | 12/1996 | Hansen et al. |
| 5,591,581 A | 1/1997 | Massey et al. |
| 5,599,668 A | 2/1997 | Stimpson et al. |
| 5,620,850 A | 4/1997 | Bamdad et al. |
| 5,637,509 A | 6/1997 | Hemmila et al. |
| 5,643,681 A | 7/1997 | Voorhees et al. |
| 5,658,443 A | 8/1997 | Yamamoto et al. |
| 5,677,196 A | 10/1997 | Herron et al. |
| 5,731,147 A | 3/1998 | Bard et al. |
| 5,780,251 A | 7/1998 | Klainer et al. |
| 5,811,526 A | 9/1998 | Davidson |
| 5,814,565 A | 9/1998 | Reichert et al. |
| 5,827,748 A | 10/1998 | Golden |
| 5,830,762 A | 11/1998 | Weindel |
| 5,832,165 A | 11/1998 | Reichert et al. |
| 5,843,692 A | 12/1998 | Phillips et al. |
| 5,863,740 A | 1/1999 | Kientsch-Engel et al. |
| 5,910,940 A | 6/1999 | Guerra |
| 5,922,537 A | 7/1999 | Ewart et al. |
| 5,922,550 A | 7/1999 | Everhart et al. |
| 5,922,615 A | 7/1999 | Nowakowski et al. |
| 5,965,305 A | 10/1999 | Ligler et al. |
| 6,030,840 A | 2/2000 | Mullinax et al. |
| 6,048,623 A | 4/2000 | Everhart et al. |
| 6,060,237 A | 5/2000 | Nygren et al. |
| 6,060,256 A | 5/2000 | Everhart et al. |
| 6,084,683 A | 7/2000 | Bruno et al. |
| 6,107,038 A | 8/2000 | Choudhary et al. |
| 6,113,855 A | 9/2000 | Buechler |
| 6,136,611 A | 10/2000 | Saaski et al. |
| 6,171,780 B1 | 1/2001 | Pham et al. |
| 6,180,288 B1 | 1/2001 | Everhart et al. |
| 6,182,571 B1 | 2/2001 | Jolliffe et al. |
| 6,200,820 B1 | 3/2001 | Hansen et al. |
| 6,203,758 B1 | 3/2001 | Marks et al. |
| 6,221,579 B1 | 4/2001 | Everhart et al. |
| 6,287,783 B1 | 9/2001 | Maynard et al. |
| 6,287,871 B1 | 9/2001 | Herron et al. |
| 6,297,060 B1 | 10/2001 | Nowakowski et al. |
| 6,312,961 B1 | 11/2001 | Voirin et al. |
| 6,331,438 B1 | 12/2001 | Aylott et al. |
| 6,362,011 B1 | 3/2002 | Massey et al. |
| 6,395,558 B1 | 5/2002 | Duveneck et al. |
| 6,399,295 B1 | 6/2002 | Kaylor et al. |
| 6,399,397 B1 | 6/2002 | Zarling et al. |
| 6,411,439 B1 | 6/2002 | Nishikawa |
| 6,416,952 B1 | 7/2002 | Pirrung et al. |
| 6,423,464 B1 | 7/2002 | Kubo et al. |
| 6,423,465 B1 | 7/2002 | Hawker et al. |

| | | | |
|---|---|---|---|
| 6,436,651 B1 | 8/2002 | Everhart et al. | |
| 6,448,091 B1 | 9/2002 | Massey et al. | |
| 6,455,861 B1 | 9/2002 | Hoyt | |
| 6,468,741 B1 | 10/2002 | Massey et al. | |
| 6,556,299 B1 | 4/2003 | Rushbrooke et al. | |
| 6,573,040 B1 | 6/2003 | Everhart et al. | |
| 6,579,673 B1 | 6/2003 | McGrath et al. | |
| 6,582,930 B1 | 6/2003 | Ponomarev et al. | |
| 6,613,583 B1 | 9/2003 | Richter et al. | |
| 6,653,151 B1 | 11/2003 | Anderson et al. | |
| 6,743,581 B1 | 6/2004 | Vo-Dinh | |
| 6,785,433 B1 * | 8/2004 | Tiefenthaler | 385/12 |
| 6,790,531 B1 | 9/2004 | Fournier | |
| 2002/0028455 A1 | 3/2002 | Laibinis et al. | |
| 2003/0027327 A1 | 2/2003 | Cunningham et al. | |
| 2004/0058385 A1 | 3/2004 | Abel et al. | |

FOREIGN PATENT DOCUMENTS

| | | |
|---|---|---|
| EP | 0420053 A1 | 4/1991 |
| EP | 0453820 A2 | 10/1991 |
| EP | 0453820 A3 | 10/1991 |
| EP | 0453820 B1 | 10/1991 |
| EP | 0539035 A2 | 4/1993 |
| EP | 0539035 B1 | 4/1993 |
| EP | 0596421 A1 | 5/1994 |
| EP | 0657737 A2 | 6/1995 |
| EP | 0657737 A3 | 6/1995 |
| EP | 1566627 A1 | 8/2005 |
| GB | 2273772 | 6/1994 |
| WO | 9005305 | 5/1990 |
| WO | 9105999 | 5/1991 |
| WO | WO 9113998 A1 | 9/1991 |
| WO | 9403496 | 2/1994 |
| WO | WO 9413835 A1 | 6/1994 |
| WO | 9415193 | 7/1994 |
| WO | WO 9609532 A1 | 3/1996 |
| WO | 9615193 | 5/1996 |
| WO | WO 9612962 A1 | 5/1996 |
| WO | 9626435 | 8/1996 |
| WO | WO 9624062 A1 | 8/1996 |
| WO | 9629629 | 9/1996 |
| WO | 9633971 | 10/1996 |
| WO | WO 9301308 A1 | 1/1998 |
| WO | 9810334 | 3/1998 |
| WO | WO 9815831 A1 | 4/1998 |
| WO | 9827417 | 6/1998 |
| WO | WO 9910742 A1 | 3/1999 |
| WO | WO 9930131 A1 | 6/1999 |
| WO | WO 9931486 A1 | 6/1999 |
| WO | WO 0050891 A1 | 8/2000 |
| WO | WO 0171322 A2 | 9/2001 |
| WO | WO 0181921 A2 | 11/2001 |
| WO | WO 0181921 A3 | 11/2001 |
| WO | WO0212865 A1 * | 2/2002 |

OTHER PUBLICATIONS

Abstract of Japanese Patent No. JP2140702 May 20, 1990.
Abstract of Japanese Patent No. JP2165933 Jun. 26, 1990.
Abstract of Japanese Patent No. JP2210302 Aug. 21, 1990.
Abstract of Japanese Patent No. JP5132640 May 28, 1993.
Abstract of Japanese Patent No. JP8062214 Mar. 8, 1996.
Article—*A New Tetradentate β-Diketonate-Europium Chelate That Can Be Covalently Bound to Proteins for Time-Resolved Fluoroimmunoassay*, Jingli Yuan and Kazuko Matsumoto, Analytical Chemistry, vol. 70, No. 3, Feb. 1, 1998, pp. 596-601.
Article—*Europium Chelate Labels in Time-Resolved Fluorescence Immunoassays and DNA Hybridization Assays*, Elefttheroid P. Diamandis and Theodore K. Christopoulos, Analytical Chemistry, vol. 62, No. 22, Nov. 15, 1990, pp. 1149-1157.

Article—*Evaluation of a Time-Resolved Fluorescence Microscope Using a Phosphorescent Pt-Porphine Model System*, E. J. Hennink, R. de Haas, N. P. Verwoerd, and H. J. Tanke, Cytometry, vol. 24, 1996, pp. 312-320.
Article—*How to Build a Spectrofluorometer*, Spex Fluorolog 3, Horiba Group, pp. 1-14.
Article—*Immunoaffinity Based Phosphorescent Sensor Platform for the Detection of Bacterial Spores*, Peter F. School, C. Brent Bargeron, Terry E. Phillips, Tommy Wong, Sala Abubaker, John D. Groopman, Paul T. Strickland, and Richard C. Benson, Proceedings of SPIE, vol. 3913, 2000, pp. 204-214.
Article—*Inert Phorphorescent Nanospheres as Markers for Optical Assays*, Jens M. Kümer, Ingo Klimant, Christian Krause, Harald Preu, Werner Kunz, and Otto S. Wolfbeis, Bioconjugate Chem., vol. 12, 2001, pp. 883-889.
Article—*Longware luminescent porphyrin probes*, Dmitry B. Papkovsky, Gelii V. Ponomarev, and Otto S. Wolfbeis, Spectrochimica Acta Part A, vol. 52, 1996, pp. 1629-1638.
Article—*Monofunctional Derivatives of Coproporphyrins for Phosphorescent Labeling of Proteins and Binding Assays*, Analystical Biochemistry, vol. 290, 2001, pp. 366-375.
Article—*Near Infrared Phosphorescent Metalloporphyrins*, Alexander P. Savitsky, Anna V. Savitskaja, Eugeny A. Lukjanetz, Svetlana N. Dashkevich, and Elena A. Makarova, SPIE, vol. 2980, pp. 352-357.
Article—*One-step all-in-one dry reagent immunoassays with fluorescent europium chelate label and time-resolved fluorometry*, Timo Lövgren, Liisa Meriö , Katja Mitrunen, Maija-Liisa Mäkinen, Minna Mäkelä , Kaj Blomberg, Tom Palenius, and Kim Pettersson, Clinical Chemistry 42:8, 1996, pp. 1196-1201.
Article—*Performance Evaluation of the Phosphorescent Porphyrin Label: Solid-Phase Immunoassay of a-Fetoprotein*, Tomaás C. O'Riordan, Aleksi E. Soini, Juhani T. Soini, and Dmitri B. Papkovsky, Analytical Chemistry, vol. 74, No. 22, Nov. 15, 2002, pp. 5845-5850.
Article—*Phosphorescent porphyrin probes in biosensors and sensitive bioassays*, D. B. Papkovsky, T. O'Riordan, and A. Soini, Biochemical Society Transactions, vol. 28, Part 2, 2000, pp. 74-77.
Article—*Polymer Based Lanthanide Luminescent Sensors for the Detection of Nerve Agents*, Amanda L. Jenkins, O. Manuel Uy, and George M. Murray, Analytical Communications, vol. 34, Aug. 1997, pp. 221-224.
Article—*Room-Temperature Phosphorescent Palladium—Porphine Probe for DNA Dtermination*, Montserrat Roza-Fernández, Maria Jesús Valencia-González, and Marta Elena Diaz-Garcia, Analytical Chemistry, vol. 69, No. 13, Jul. 1, 1997, pp. 2406-2410.
*Magnetic Microparticles*, Polysciences, Inc. Technical Data Sheet 438, 2 pages.
*Working With FluoSpheres® Flurosent Microspheres*, Properties and Modifications, Product Information from Molecular Probes, Mar. 9, 2001, pp. 1-5.
PCT Search Report for PCT/US03/11757 May 4, 2004.
PCT Search Report for PCT/US03/11757 May 6, 2004.
Article—*Chromosphere-assisted laser inactivation of proteins is mediated by the photogeneratio of free radicals*, Joseph C. Liao, Johann Roider, and Daniel G. Jay, Proc. Natl. Acad. Sci. USA, vol. 91, Mar. 1994, pp. 2659-2663.
Article—*Laser-Mediated protein Inactivation for Target Validation*, Jens Niewöhner, Susanne Rubenwolf, Elisabeth Meyer, and Fritz Rudert, Jul./Aug. 2001, pp. 28-33.
Introduction to Fluorscene Techniques, Molecular Probes, 13 pages.
PCT Search Report for PCT/US03/29005.
EPO Search Report, Aug. 29, 2003.
U.S. Appl. No. 10/256,278, filed Sep. 26, 2002.
Letter to the Editors, Comment on the Predication of Segregation to Alloy Surfaces, Copyright-1977.
Prediction of Segregation to Alloy Surfaces From Bulk Phase Diagrams, Physical Review Letters, Vol. 37, No. 21, Nov. 22, 1976.
Orientation Dependence of Surface Segregation in a Dilute Ni-Au Alloy, Research Staff, Ford Motor Company, Dearborn, MI, Received Sep. 19, 1977; Accepted Nov. 18, 1977.

Volume Phase Transition of N-Alkylacrylamide Gels, Department of Molecular Chemistry and Engineering, Tohoku University, Advances on Polymer Science Vol. 109, 1993.

Molecular Design of Temperature-Responsive Polymer as Intelligent Materials, Institute of Biomedical Engineering, Tokyo Women'Medical College, Advances on Polymer Science Vol. 110.

Molecular Gradients of w-Substituted Alkanethiols on Gold Preparation and Characterization, Laboratory of Applied Physics, 1995 American Chemical Society, Jun. 6, 1995.

Acoustic Plate Waves for Measurement of Electrical Properties of Liquids, Mirochemical Journal 43, 155-164, Jan. 31, 1991.

Analysis of Electrical Equivalent Circuit of Quartz Crystal Resonator Loaded With Viscous Conductive Liquids, Journal of Electroanalytical Chemistry 379 (1994) 21-33, Apr. 12, 1994.

Quartz Crystal Resonators as Sensors in Liquids Using the Acoustoelectric Effect, Anal. Chem. 1994, 66, 1995-1964.

Features of Gold Having Micrometer to Centimeter Dimensions Can Be Formed Through A Combination of Stamping With an Elastomeric Stamp and Alkanethol "Ink" Following By Chemical Etching, Appl. Phys. Lett. 63 (14), Oct. 4, 1993.

Photolithography of Self Assembled Monolayers: Optimization of Protecting Roups By an Electoanalytical Method, Can. J. Chem; 2509-2517 (1996).

Order in Microcontact Printed Self-Assembled Monolayers, Contributions of The IBM Research Division, Nov. 26, 1996.

Combining Patterned Self-Assembled Monolayers of Alkanthiolates on Gold With Anisotropic Etching of Silicon to Generate Controlled Surface Morphologies, J. Electrochem. Soc., vol. 142, No. 2, Feb.., 1995.

109 Advances in Polymer Science, Responsive Gels: Volume Transitions I, Springer Verlag Berlin Heidelberg 1993.

110 Advances in Polymer Science, Responsive Gels: Volume Transitions II, Springer Verlag Berlin Heidelberg 1993.

Intelligent Gels, Scientific American May 1993.

Volume Phase Transition and related Phenomena of Polymer Gels, Advances In Polymer Science, vol. 109, Springer-Verlag Berlin Heidelberg 1993.

Novel Applications For Stimulus-Sensitive Polymer Gels In The Preparation of Functional Immobilized Biocatalysts, Advances In Polymer Science, vol. 110, Verlag Berlin Heidelberg 1993.

Stimuli-Responsive Polymer Gels and Their Application To Chemomechanical Systems, Prg. Polym. Sci. vol. 18, 187-226, 1993.

Electrical Surface Perturbation of A Piezoelectric Acoustic Plate Mode By A Conductive Liquid Loading, IEEE Transactions On Ultrasonics, Ferroelectrics, and Frequency Control, vol. 39, No. 4, Jul. 1992.

On The Use of ZX-LiNbO$_3$ Acoustic Plate Mode Devices as Detectors For Dilute Electrolytes, Sensors and Actuators B. 9 (1992) 97-112.

Probing of Strong and Weak Electrolytes With Acoustic Wave Fields, Sensors and Actuators B. 9 (1992) 155-162.

Using Micromachining, Molecular Self-Assembly, and Wet Etching To Fabricate 0.1-1 um Scale Structures of Gold and Silicon, Chemistry of Materials, 1994.

Patterned Self-Assembled Monolayers Formed By Microcontact Printing Direcr Selective Metalization by Chemical Vapor Deosition On Planar and Nonplanar Substrates, Langmuir 1995, 11, 3024-3026.

Self-Assembled Monolayers of Long-Chain Hydroxamic Acis on The Native Oxides of Metals, Langmuir, 1995, 11.

Microfabrication by Microcontact Printing of Self-Assembled Monolayers, VCH Verlagsgesellschaf T mbH 1884.

Patterned Condensation Figures As Optical Diffraction Gratings, American Association For The Advancement of Science, 1994.

Stimuli-Responsive Poly(N-Isoproplylacrylamide). Photo—and Chemical-Induced Phase Transitions, Advances In Polymer Science No. 110, 1993.

Quantitative Prediction of Surface Segregation, Journal of Catalysis 57, 450-457 (1970).

Sensing Liquid Properties With Thickness-Shear Mode Resonators, Sensors and Actuators A 44 (1944) 209-218.

Direct Observation of Strept A Vidin Specifically Adsorbed on Biotin-Functionalized Self-Assembled Monolayers With The Scanning Tunneling Microscope, Angew Chem. Int. Ed. Engl. 30 (1991) No. 5.

New Approach To Producing Patterned Biomolecular Assemblies, Journal of The American Chemical Society, 1992.

The Biotin-(Strept) A Vidin System: Principles and Applications In Biotechnology, Clinical Chemistry vol. 37, No. 5, 1991.

Fabrication of Surfaces Resistant To Protein Adsorption and Application To Two-Dimensional Protein Patterning, Analytical Biochemistry 208, 197-205 (1993).

Patterning Self-Assembled Monolayers Using Microcontact Printing: A New Technology For Biosensor?, Department of Chemistry, Harvard University.

Photosensitive Self-Assembled Monolayers On Gold: Photochemistry of Surface-Confined Aryl Azide and Cyclopentadienylmanganese Tricarbonyl, Ameican Chemical Society, 1994.

Generation of Electrochemically deposited Metal Patterns By Means of Electron Beam (Nano)Lithography of Self-Assembled Monolayer Resists, American Institute of Physics, 1994.

Selective Electrochemical Deposition of Polyaniline Via photopatterning of A Onolayer-Modified Substrate, American Chemical Society 1994.

Pattern Transfer of Electron Beam Modified Self-Assembled Monolayers for High-Resolution Lithography, J. Vac. Sci. Technol. B 13(3) May/Jun. 1995.

Patterned Functionalization of Gold and Single Crystal Silicon Via PhotoChemical Reaction of Surface-Confined Derivatives of ($N^5$ $C_5H_5$)Mn(CO)$_3$, American Chemical Society 1991.

Photopatterning and Selective Electroles Metallization of Surface-Attached Ligands, American Chemical Society 1993.

Control of The Shape of Liquid Lenses On A Modified Gold Surface Using an Applied lectrical Potential Across A Self-Assembled Monolayer, American Chemical Society 1995.

Fabrication of A Patterned Electrically Conducting Polypyrrole Using A Self-Assembled Monolayer: A Route To All-Organic Circuits, American Chemical Society 1995.

Wet Chemical Approcahes To The Characterization of Organic Surfaces: Self-Assembled Monolayers, Wetting, and The Physical-Organic Chemistry of The Solid-Liquid Interface, Department of Chemistry, Harvard University, 1989.

UV Photpatterning of Alkanethiolate Monolayers Self-Assembled On Gold and Silver, American Chemical Society 1993.

The Use of Self-Assembled Monolayers and A Selective Etch To Generate Patterned Gold Features, American Chemical Society 1992.

Use of a Patterned Self-Assembled Monolayer to Control The Formation of A Liquid Resist Pattern On A Gold Surface, American Chemical Society 1995.

Self-Organization of Organic Liquids On Patterned Self-Assembled Monolayers of Alkanethiolates On Gold, Langmuir 1994.

Self-Assembled Monolayer Electron Beam Resist On GaAS, American Institute of Physics 1993.

Manipulation of The Wettability of Surface On The 0.1—To 1—Micrometer Scale Through Micromachinig and Molecular Self-Assembly, Science, vol. 257, Sep. 1992.

Comparison of The Structures and Wetting Properties of Self-Assembled Monolayers on the Coinage Metal Surfaces, Cu, Ag, Au, American Chemical Society, 1991.

Self-Assembled Monolayer Films For Nanofabrication, Mat. Res. Soc. Symp. Proc. vol. 380, 1995 Materials Reserach Society.

Patterned Metal Electrodeposition Using an Alkanthiolate Mask, J. Electrochem. Soc. vol. 142, No. 11, Nov. 1995.

Biospecific Adsorption of Carbonic Anhydrase To Self-Assembled Monolayers of Alkanthiolates That Present Benzenesulfonamide Groups On Gold, American Chemical Society, 1995.

Microcontact Printing of Octadecylsiloxane On The Surface Of Silicon Dioxide and Its Application In Microfabrication, American Chemical Society 1995.

Attempts To Mimic Docking Processes of The Immune System: recognition-Induced formation of Protein Multilayers, Science, Vol. 262, Dec. 10, 1993.

Mechanical resonance Gas Sensors With Piezoelectric Excitation and Detection using PVDF Polymer Foils, Elsevier Sequoia 1992.

Application of Rod-Like Polymers With Ionophores As Langmuir-Blodgett Membranes For Si-Based Ion Sensors, Elsevier Sequoia 1992.

Patterning Self-Assembled Monolayers: Applications In Materials Science, Department of Chemistry, Harvard university, feb. 18, 1994.

Optical Biosensor Assay, (OBA) Clinical Chemistry, vol. 37, No. 9, 1991.

U.S. Appl. No. 10/139,018, filed May 3, 2002.

U.S. Appl. No. 10/138,882, filed May 3, 2002.

U.S. Appl. No. 10/138,677, filed May 3, 2002.

U.S. Appl. No. 10/138,598, filed May 3, 2002.

U.S. Appl. No. 10/139,02, filed May 3, 2002.

U.S. Appl. No. 10/139,013, filed May 3, 2002.

Article—*Diffraction-Based Cell Detection Using a Microcontact Printed Antibody Grating*, St. John et al., Analytical Chemistry, vol. 70, No. 6, Mar. 15, 1998, pp. 1108-1111.

Article—*Micro-Scale Patterning of Biological Molecules*, Pritchard et al., Angew. Chem. Int. Ed. Engl., vol. 34, No. 1, 1995, pp. 91-93.

Article—*Oxidation of Self-Assembled Monolayers by UV Light with a Wavelength of 254 nm*, Breweer et al., J. Am. Chem. Soc., vol. 123, 2001, pp. 4089-4090.

\* cited by examiner

ENHANCED DIFFRACTION-BASED BIOSENSOR DEVICES

TECHNICAL FIELD OF THE INVENTION

The present invention relates generally to the field of detecting analytes in a medium, and more particularly to an improved analyte-specific diffraction based diagnostic sensor to indicate the presence of the analyte in a medium.

BACKGROUND

There are many systems and devices available for detecting a wide variety of analytes in various media. Many of the prior systems and devices are, however, relatively expensive and require a trained technician to perform the test. A need has been recognized in the art for biosensor systems that are easy and inexpensive to manufacture, and are capable of reliable and sensitive detection of analytes. Reference is made, for example, to U.S. Pat. Nos. 5,922,550; 6,060,256; and 6,221,579 B1.

Optical diffraction based biosensors have gained acceptance in the art in that they are relatively sensitive, inexpensive, and easy to use. Various advances have been made for producing such biosensors. For example, U.S. Pat. No. 5,512,131 to Kumar, et al., describes a device that includes a polymer substrate having a metal coating. An analyte specific receptor layer is stamped onto the coated substrate. A diffraction pattern is generated when an analyte binds to the device, and the device is exposed to light. A visualization device, such as a spectrometer, is then used to determine the presence of the diffraction pattern. However, a drawback to this type of device is the fact that the diffraction pattern is not discernible by the naked eye and, thus, a complex visualization device is needed to view the diffraction pattern. Also, the device is generally not able to detect smaller analytes that do not produce a detectable diffraction pattern.

U.S. Pat. No. 5,922,550 describes a biosensor having a metalized film upon which is printed (contact printed) a specific predetermined pattern of an analyte-specific receptor. The receptor materials are bound to the self-assembling monolayer, and are specific for a particular analyte or class of analytes. Attachment of a target analyte that is capable of scattering light to select areas of the metalized plastic film upon which the receptor is printed causes diffraction of transmitted and/or reflected light. A diffraction image is produced that can be easily seen with the eye or, optionally, with a sensing device.

U.S. Pat. No. 6,060,256 describes a similar device having a metalized film upon which is printed a specific predetermined pattern of analyte-specific receptor. The '256 patent is not limited to self-assembling monolayers, but teaches that any receptor which can be chemically coupled to a surface can be used. The invention of the '256 patent uses methods of contact printing of patterned monolayers utilizing derivatives of binders for analytes (e.g. microorganisms). One example of such a derivative is a thiol. The desired binding agent can be thiolated antibodies or antibody fragments, proteins, nucleic acids, sugars, carbohydrates, or any other functionality capable of binding an analyte. The derivatives are chemically bonded to metal surfaces such as metalized polymer films, for example via a thiol.

Other types of detection principles are also known for application in biosensors, including fluorescence, chemiluminescence, phosphorescence, colorometric, and radiometric based devices. Each type of device has its own advantages and disadvantages. For example, U.S. Pat. No. 5,482,830 to Bogart, et al., describes a colorometric based device that includes a substrate having an optically active surface exhibiting a first color in response to light impinging thereon. This first color is defined as a spectral distribution of the emanating light. The substrate also exhibits a second color which is different from the first color. The second color is exhibited in response to the same light when the analyte is present on the surface. The change from one color to another can be measured either by use of an instrument, or by the naked eye. A drawback with the device is, however, the relatively high cost of the device and problems associated with controlling the various layers that are placed on the wafer substrate.

Although optical diffraction based biosensors have particular advantages, it is also recognized that such biosensors can be improved with respect to reliability and performance.

The present invention relates to an optical diffraction based biosensor incorporating at least one other type of detection mechanism. The resulting hybrid biosensor has distinct advantages over a purely diffraction based biosensor in certain applications.

SUMMARY OF THE INVENTION

Objects and advantages of the invention will be set forth in part in the following description, or may be obvious from the description, or may be learned through practice of the invention.

The present invention provides a relatively inexpensive yet sensitive biosensor device, a method for producing such biosensor devices, and a method for detecting analytes of interest present in a medium. Biosensors according to the invention are hybrid biosensors combining optical diffraction with another detection tag, such as fluorescence. Each detection method is capable of acting essentially as an internal control on the other method. Biosensors according to the present invention can detect and quantify analytes of interest in a medium, and provide increased reliability and performance.

The biosensor includes a substrate member upon which a layer containing an analyte specific receptive material (i.e., biomolecules) has been patterned onto a surface of the substrate member. The substrate may be any one of a wide variety of suitable materials, including plastics, metal coated plastics and glass, functionalized plastics and glass, silicon wafers, foils, glass, etc. Desirably, the substrate is flexible, such as a polymeric film, in order to facilitate the manufacturing process. The receptive material layer may be applied by any number of known techniques, including dipping, spraying, rolling, and any other technique wherein the receptive material layer can be applied generally uniformly onto the test surface of the substrate. The invention also includes contact printing methods of applying the coating, as long as such methods are conducted in a manner to prevent inconsistent inking and contamination from contact during the initial coating process. The receptive material layer may be defined in a specific pattern on the substrate, either directly or as a patterned self-assembled monolayer having receptive material bound thereto. For example, self assembled monolayers of thiol-containing molecules on metal (e.g., gold) coated substrates form the basis for a variety of biosensors. Reference is made for example to U.S. Pat. No. 5,922,550, the entire disclosure of which is incorporated herein in its entirety for all purposes.

The receptive material may also be defined on the substrate member as a pattern of active analyte-specific regions in a photo-masking process. For example, a generally uniform coating or layer of receptive material may be applied to the entire substrate surface. A layer or coating of a blocking agent may be applied over the receptive material layer. A mask having any desired pattern of shielded areas and exposed areas (blank, transparent, or translucent areas) is then placed over the substrate member. The mask and substrate combination are then exposed to a particular stimulus (e.g., light) selected to activate the blocking agent under the exposed areas of the mask or directly inactivate the receptive material. The exposed areas thus define a pattern of inactive areas and the areas under the shielded areas of the mask define a pattern of active receptive material areas. After removal of the mask, the inactivated blocking agent is disassociated from the receptive material, for example in a subsequent rinsing or washing process. Other photo-masking techniques are described in detail in co-pending and commonly owned U.S. application Ser. Nos. 10/139,013; 10/139,025; 10/139,018; 10/138,598; 10/138,882; and 10/138,677, such applications incorporated herein in their entirety for all purposes.

Upon subsequent exposure of the biosensor to a medium containing an analyte of interest, the analyte binds to the receptive material. If the analyte molecules are large enough and have a sufficient refractive index, the biosensor will then diffract transmitted light in a diffraction pattern corresponding to the pattern of receptive material defined on the substrate. The diffraction pattern may be visible to the naked eye or, optionally, viewed with a sensing device.

In the case where an analyte does not scatter visible light because the analyte is too small or does not have an appreciable refractive index difference compared to the surrounding medium, it is known to use diffraction-enhancing elements, such as polymer microparticles. Reference is made, for example, to U.S. Pat. No. 6,221,579 for a detailed discussion of the use of diffraction enhancing particles in diffraction based biosensors. These microparticles are coated with a binder or receptive material that also specifically binds to the analyte of interest. Upon subsequent coupling of the analyte to both the patterned biomolecules in the receptive material layer as well as the microparticles, a diffraction image is produced which can be easily seen with the eye or, optionally, with a sensing device.

In another embodiment of the present invention, nutrients for a specific class of microorganisms can be incorporated into the receptive material layer. In this way, very low concentrations of microorganisms can be detected by first contacting the biosensor having nutrient enhanced receptive material with the test sample, and then incubating the biosensor under conditions appropriate for the growth of the bound microorganism. The microorganism is allowed to grow until there are enough organisms to form a diffraction pattern.

In accordance with aspects of the present invention, the diffraction based biosensor includes at least one other type of analyte detection mechanism ("detection tag"). The additional detection tag may be, for example, fluorescent, colorometric, radiometric, or chemiluminescent based. In principle, the analyte of interest is "tagged" with an element or substance that emits a measurable parameter (physical characteristic) in addition to the optical diffraction characteristic of the analyte. This additional measurable parameter may be, for example, color, fluorescence, radiation, chemical induced luminescence, etc. This unique combination in a diffraction based biosensor may provide distinct advantages. For example, because each detection method is essentially independent on the other, they act as an internal "control" to each other. In the case of a diffraction/fluorescent hybrid sensor wherein fluorescent labeled beads are used as diffraction enhancing elements, the beads would result in both diffraction of light and a measurable fluorescence intensity. The fluorescence parameter thus acts as a "control" or a "check" on the diffraction parameter, and vice versa. Also, with this approach, both qualitative and quantitative measurements may be made of the analyte present in the given test medium. The optical diffraction parameter can provide a qualitative assessment of a "yes" or "no" answer of the formation of an immune complex from the presence of the analyte of interest, while the magnitude or intensity of fluorescence emission could indicate quantitatively "how much" of the immune complex was formed. The amount of immune complex could then be correlated to the amount of analyte present in the test medium.

The present invention provides a low-cost, disposable biosensor which can be mass produced. The biosensors of the present invention can be produced as a single test for detecting an analyte or it can be formatted as a multiple test device. The uses for the biosensors of the present invention include, but are not limited to, detection of chemical or biological contamination in garments, such as diapers, the detection of contamination by microorganisms in prepacked foods such as fruit juices or other beverages, and the use of the biosensors of the present invention in health diagnostic applications such as diagnostic kits for the detection of antigens, microorganisms, and blood constituents. It should be appreciated that the present invention is not limited to any particular use or application.

These and other features and advantages of the present invention will become apparent after a review of the following detailed description of the disclosed embodiments.

DETAILED DESCRIPTION

Figure 1:
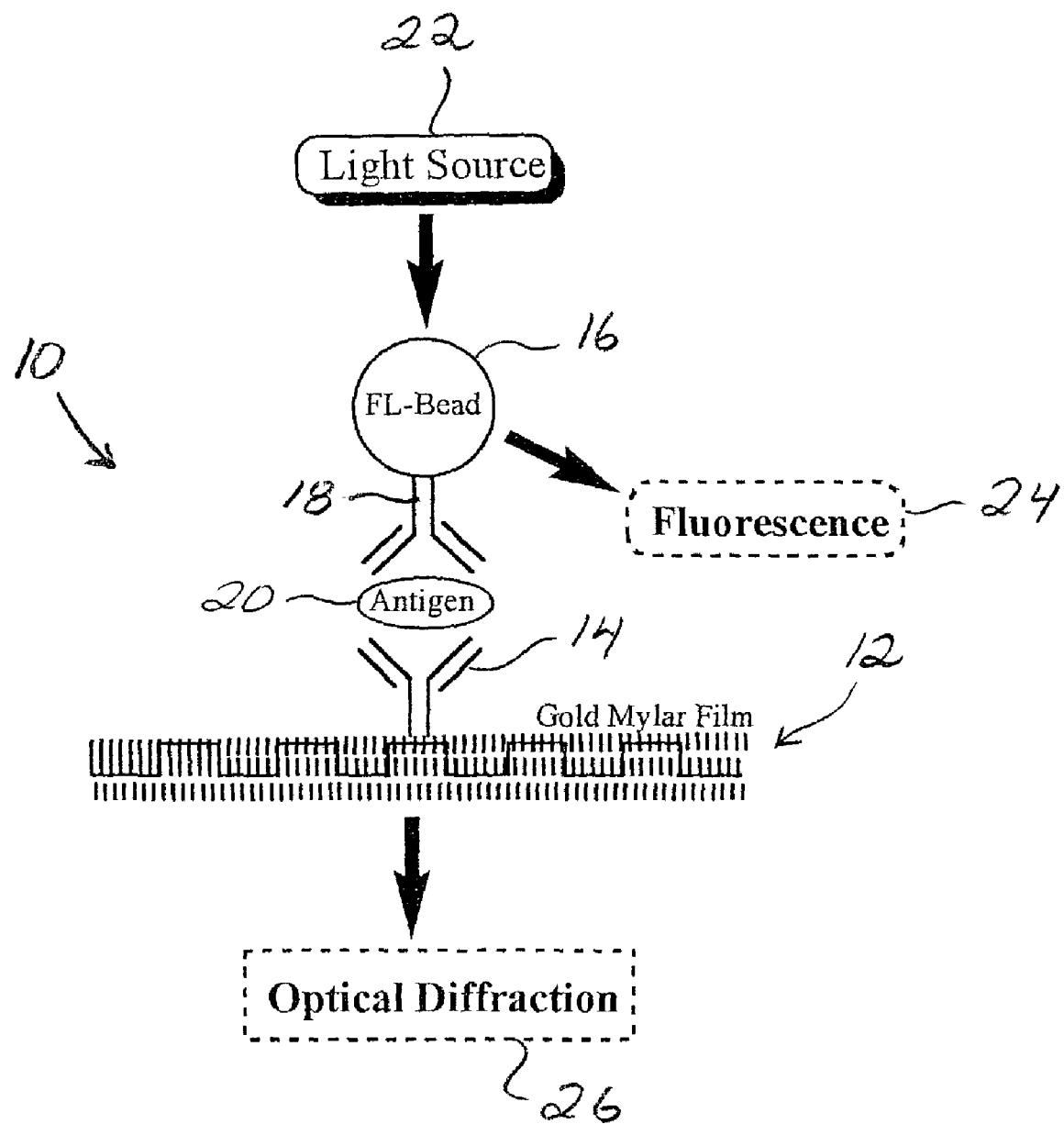
FIG. 1 is a schematic representation of a biosensor according to the present invention.

The invention will now be described in detail with reference to particular embodiments thereof. The embodiments are provided by way of explanation of the invention, and not meant as a limitation of the invention. For example, features described or illustrated as part of one embodiment may be used with another embodiment to yield still a further embodiment. It is intended that the present invention includes these and other modifications and variations as come within the scope and spirit of the invention.

The present invention features improved diffraction-based biosensing devices, and methods for using such biosensing devices, for detecting and quantifying the presence and/or amount of an analyte of interest within a medium. The analytes that can be detected by the present invention include, but are not limited to, microorganisms such as bacteria, yeasts, fungi, proteins, small molecules, nucleic acids, and viruses. The biosensing devices according to the invention are relatively inexpensive and have advantages over conventional diffraction-based biosensors.

By "diffraction" it is meant the phenomenon observed when waves are obstructed by obstacles caused by the disturbance spreading beyond the limits of the geometrical shadow of the object. The effect is marked when the size of the object is of the same order as the wavelength of the waves. In the present invention, the obstacles are analytes (with or without attached microparticles) and the waves are light waves.

The present invention comprises, in broad terms, a process for enhancing diffraction-based biosensors by providing an additional and separately measurable detection tag. The additional detection tag may be, for example, any one or combination of fluorescent, colorimetric, radiometric, or chemiluminescent based substances that yield a measurable and detectable parameter in addition to diffraction caused by attachment of an analyte of interest to the biosensor. This parameter may give a quantitative indication of the amount of analyte present in a test medium in addition to the qualitative indication from diffraction of transmitted or reflected light. In a particularly advantageous embodiment according to the invention, the detection tag is a fluorescent substance, and in one particular embodiment the detection tag is fluorescent-labeled microspheres that also serve as diffraction enhancing elements. For purposes of explanation of the invention, embodiments using a fluorescent detection tag, such as fluorescent microspheres, will be discussed herein. It should be understood, however, that this is for illustrative purposes only, and the invention is not limited to fluorescent based detection tags.

The present invention includes applying an analyte-specific receptive material onto a substrate, such as a metal coated polymer film, to produce single-use, disposable biosensors. For smaller analytes that do not readily produce a diffraction pattern, diffraction enhancing elements are provided to increase the diffraction efficiency of the biosensor, thereby making it possible to detect any number of different analytes. These diffraction enhancing elements may include the additional detection tag. For example, the diffraction enhancing elements may be fluorescent microspheres coated with a receptive material specific to the analyte. Upon attachment of the analyte of interest to the receptive material on the substrate, either directly or in combination with diffraction enhancing elements, diffraction of transmitted and/or reflected light occurs in a detectable pattern corresponding to the pattern of the receptive material on the substrate. In addition, the fluorescence emitted by the microspheres may be detected and measured as a separate indication of the presence and quantity of analyte present.

Certain analytes of interest, for example yeast, fungi, or bacterium, are large enough to act as diffraction elements for visible light when deposited in organized patterns on the substrate. As described herein, these "larger" analytes may be tagged directly with fluorescent tracers. However, as mentioned, smaller analytes, such as certain viruses, proteins, molecules, hormones, steroids, drug metabolites, and nucleic acids, are only capable of acting as suitable diffraction elements if they are also bound to a diffraction enhancing element. These elements may be made specific for the smaller analytes by coating the element particle with a receptor material that specifically binds to the analyte of interest. This receptor material binds to an epitope on the analyte that is different from the epitope used to bind the analyte to the receptive material on the substrate.

A variety of methods may be used to attach the receptor material onto the diffraction enhancing element. These methods include, but are not limited to, simple physisorption to a hydrophobic particle (e.g., binding a protein onto polystyrene particles); binding using a protein A or protein G linker; binding using a streptavidin or avidin-biotin binder; or binding using covalent attachment. With one particularly desirable embodiment, carbodiimide coupling is used to couple a proteinaceous receptor to carboxylated fluorescent-labeled particles.

The fluorescent-labeled particles are desirably spherical in shape, but the structural and spatial configuration of the particles is not critical to the present invention. For instance, the particles could be slivers, ellipsoids, hollow, cubes, random shape and the like. A desirable particle size ranges from a diameter of approximately 0.1 micron to 50 microns, desirably between approximately 0.1 micron and to 2.0 microns. The composition of the particle is not critical to the present invention.

Thus, in one embodiment of the method for detecting a relatively small analyte, such as viral particles, the subject medium is first exposed to the fluorescent-labeled diffraction enhancing particles, such as carboxylated fluorescent-labeled particles, which were previously bound to receptors having an affinity for the analyte. The analytes (e.g., viral particles) couple to the diffraction enhancing particles by way of the receptors binding to an epitope of the analyte. The diffraction enhancing particles may be washed, and are then exposed to the substrate (e.g., a metalized polymer film) having the analyte-specific receptive material applied thereto. The analyte and attached diffraction enhancing particles will bind to the receptive material on the substrate by way of the receptive material binding to a different epitope of the analyte. The analyte and diffraction enhancing particles are thus immobilized on the substrate in a pattern corresponding to the pattern of the receptive material layer. Because the bound analyte and diffraction enhancing particles will cause diffraction of visible light, a diffraction pattern is formed upon exposure of the substrate to transmitted or reflected light indicating the presence of the analyte.

In addition, the fluorescent-labeled diffraction enhancing elements will also respond to the same or a different light by emitting energy in the form of fluorescence. Fluorescence is the result of a three-stage process that occurs in certain molecules called fluorophores or fluorescent dyes. In the first stage, energy is supplied by an external source such as an incandescent lamp or a laser and absorbed by the fluorophore, creating an excited electronic singlet state. This process distinguishes fluorescence from chemiluminescence, in which the excited state is produced by a chemical reaction. In the second stage, the excited state exists for a finite time during which the fluorophore undergoes vibrational or conformational changes and is also subject to a multitude of possible interactions with its molecular environment. During this time, the energy of the excited state is partially dissipated, yielding a relaxed state from which fluorescence emission originates. The third stage is the fluorescence emission stage wherein energy is emitted, returning the fluorophore to its ground state. The emitted energy is lower than its excitation energy (light or laser), and thus of a longer wavelength. This shift or difference in energy or wavelength allows the emission energy to be detected and isolated from the excitation energy.

Fluorescence detection requires wavelength filtering or time-resolved methodology to isolate the emission photons from the excitation photons, and a detector that registers emission photons and produces a recordable output, usually as an electrical signal or a photographic image. There are generally four recognized types of detectors: spectrofluorometers and microplate readers; fluorescence microscopes; fluorescence scanners; and flow cytometers. A suitable fluorescence detector for use with the present biosensors is a FluoroLog III Spectrofluorometer with a front face mode. Based on examples with the microspheres described below, this instrument is set with excitation of 570 nm and emission at 605 nm, with integration time ranges from about 0.2 to about 0.5 seconds.

Applicants have found that a particularly well suited fluorescent substance for use in biosensors according to the present invention are 0.5 micron diameter carboxylated fluorescent particles from Molecular Probes of Eugene, Oreg. (known as FluoSphere fluorescent microspheres).

In an alternative embodiment, the analyte of interest may be detected by first exposing the substrate to the medium containing the analyte and causing the analyte to bind to the analyte specific receptive material layer. Next, a solution containing the diffraction enhancing fluorescent particles (bound to receptors having an affinity for the analyte of interest) is contacted with the substrate having the analyte of interest bound thereto. The particles then bind to the analyte and will cause diffraction of visible light in a diffraction pattern corresponding to the pattern of the receptive material and bound analyte indicating the presence of the analyte. In addition, the fluorescent-labeled diffraction enhancing elements will also respond to the light by emitting energy in the form of visible and measurable fluorescence.

In still a further embodiment, the biosensor, the diffraction enhancing fluorescent-labeled particles, and the medium containing the analyte of interest may be admixed simultaneously. This will result in a combination of the binding procedures discussed above. Some of the analytes will first bind with a diffraction enhancing element prior to binding to the substrate. Other analytes will first bind with the substrate and then bind with an element particle.

In the case of relatively larger analytes that adequately result in diffraction of transmitted or reflected light without attached enhancing elements, it may not be feasible or desirable to use fluorescent-labeled microspheres as the additional tag element. It is, however, contemplated by the inventors to use analyte-specific fluorescent tracers or dyes to tag the "larger" analytes. For example, lipophilic tracers are conventionally used to label cells, organelles, liposomes, viruses, and lipoproteins. These particular types of dyes diffuse through the cell membrane and essentially stain the entire cell, even if the dye is applied locally. Carbocyanines and aminostyryl dyes are examples of lipophilic tracers.

Certain other types of larger analytes, such as yeast and fungi, contain carbohydrate moieties on their surface. Fluorescent-labeled lectins will to bind to the carbohydrates and generate both fluorescence and enhance the diffraction signals.

The analytes that are contemplated as being detected using the present invention include, but are not limited to, bacteria; yeasts; fungi; viruses; rheumatoid factor; antibodies, including, but not limited to IgG, IgM, IgA, IgD, and IgE antibodies; carcinoembryonic antigen; streptococcus Group A antigen; viral antigens; antigens associated with autoimmune disease, allergens, tumor antigens; streptococcus Group B antigen, HIV I or HIV II antigen; or host response (antibodies) to these and other viruses; antigens specific to RSV or host response (antibodies) to the virus; antigen; enzyme; hormone; polysaccharide; protein; lipid; carbohydrate; drug or nucleic acid; *Salmonella* species; *Candida* species, including, but not limited to *Candida albicans* and *Candida tropicalis; Neisseria meningitides* groups A, B, C, Y and W sub 135, *Streptococcus pneumoniae, E. coli, Haemophilus influenza* type A/B; an antigen derived from microorganisms; PSA (prostate specific antigen), LH (Luteinizing Hormone) and CRP (C-reactive protein) antigens; a hapten; a drug of abuse; a therapeutic drug; an environmental agent; and antigens specific to Hepatitis. In broad terms, the "analyte of interest" may be thought of as any agent whose presence or absence from a biological sample is indicative of a particular health state or condition.

It is also contemplated that nutrients for a specific class of microorganism can be incorporated into the receptive material layer. In this way, very low concentrations of microorganisms can be detected by exposing the biosensor of the present invention with the nutrients incorporated therein to the suspect medium and then incubating the biosensor under conditions appropriate for the growth of the bound microorganism. The microorganisms are allowed to grow until there are enough organisms to form a diffraction pattern. Of course, in some cases, the microorganism is present or can multiply enough to form a diffraction pattern without the presence of a nutrient in the active receptive material areas.

The receptive material is characterized by an ability to specifically bind the analyte or analytes of interest. The variety of materials that can be used as receptive material is limited only by the types of material which will combine selectively (with respect to any chosen sample) with a secondary partner. Subclasses of materials which fall in the overall class of receptive materials include toxins, antibodies, antibody fragments, antigens, hormone receptors, parasites, cells, haptens, metabolites, allergens, nucleic acids, nuclear materials, autoantibodies, blood proteins, cellular debris, enzymes, tissue proteins, enzyme substrates, coenzymes, neuron transmitters, viruses, viral particles, microorganisms, proteins, polysaccharides, chelators, drugs, aptamers, peptides, and any other member of a specific binding pair. This list only incorporates some of the many different materials that can be coated onto the substrate surface to produce a thin film assay system. Whatever the selected analyte of interest is, the receptive material is designed to bind specifically with the analyte of interest.

The matrix or medium containing the analyte of interest may be a liquid, a solid, or a gas, and can include a bodily fluid such as mucous, saliva, urine, fecal material, tissue, marrow, cerebral spinal fluid, serum, plasma, whole blood, sputum, buffered solutions, extracted solutions, semen, vaginal secretions, nasal secretions, tears, pericardial, gastric, peritoneal, pleural, or other washes and the like. The analyte of interest may be an antigen, an antibody, an enzyme, a DNA fragment, an intact gene, a RNA fragment, a small molecule, a metal, a toxin, an environmental agent, a nucleic acid, a cytoplasm component, pili or flagella component, protein, polysaccharide, drug, or any other material. For example, receptive material for bacteria may specifically bind a surface membrane component, protein or lipid, a polysaccharide, a nucleic acid, or an enzyme. The analyte which is specific to the bacteria may be a polysaccharide, an enzyme, a nucleic acid, a membrane component, or an antibody produced by the host in response to the bacteria. The presence or absence of the analyte may indicate an infectious disease (bacterial or viral), cancer or other metabolic disorder or condition. The presence or absence of the analyte may be an indication of food poisoning or other toxic exposure. The analyte may indicate drug abuse or may monitor levels of therapeutic agents.

One of the most commonly encountered assay protocols for which this technology can be utilized is an immunoassay. However, the general considerations apply to nucleic acid probes, enzyme/substrate, and other ligand/receptor assay formats. For various formats of immunoassays, an antibody may serve as the receptive material or it may be the analyte of interest. The receptive material, for example an antibody or an antigen, must form a stable, relatively dense, reactive layer on the substrate surface of the test device. If an antigen is to be detected and an antibody is the receptive material, the antibody must be specific to the antigen of interest; and the antibody (receptive material) must bind the antigen (analyte) with sufficient avidity that the antigen is retained at the test surface. In some cases, the analyte may not simply bind the receptive material, but may cause a detectable modification of the receptive material to occur. This interaction could cause an increase in mass at the test surface or a decrease in the amount of receptive material on the test surface. An example of the latter is the interaction of a degradative enzyme or material with a specific, immobilized substrate. In this case, one would see a diffraction pattern before interaction with the analyte of interest, but the diffraction pattern would disappear if the analyte were present. The specific mechanism through which binding, hybridization, or interaction of the analyte with the receptive material occurs is not important to this invention, but may impact the reaction conditions used in the final assay protocol.

In addition to producing a simple diffraction image, patterns of analytes can be such as to allow for the development of a holographic sensing image and/or a change in visible color. Thus, the appearance of a hologram or a change in an existing hologram will indicate a positive response. The pattern made by the diffraction of the transmitted light can be any shape including, but not limited to, the transformation of a pattern from one pattern to another upon binding of the analyte to the receptive material. In particularly preferred embodiments, the diffraction pattern becomes discernible in less than one hour after contact of the analyte with the biosensing device of the present invention.

Any one of a wide variety of materials may serve as the substrate to which the receptive material is applied. Such materials are well known to those skilled in the art. For example, the substrate may be formed of any one of a number of suitable plastics, metal coated plastics and glass, functionalized plastics and glass, silicon wafers, foils, glass, etc. Rather than requiring a rigid substrate, it has been found that thermoplastic films are quite suitable. Such films include, but are not limited to, polymers such as: polyethylene-terephthalate (MYLAR®), acrylonitrile-butadiene-styrene, acrylonitrile-methyl acrylate copolymer, cellophane, cellulosic polymers such as ethyl cellulose, cellulose acetate, cellulose acetate butyrate, cellulose propionate, cellulose triacetate, polyethylene, polyethylene—vinyl acetate copolymers, ionomers (ethylene polymers) polyethylene-nylon copolymers, polypropylene, methyl pentene polymers, polyvinyl fluoride, and aromatic polysulfones. Preferably, the plastic film has an optical transparency of greater than 80%. Other suitable thermoplastics and suppliers may be found, for example, in reference works such as the Modern Plastics Encyclopedia (McGraw-Hill Publishing Co., New York 1923–1996).

In one embodiment of the invention, the thermoplastic film may have a metal coating. The film with metal coating thereon may have an optical transparency of between approximately 5 percent and 95 percent. A more desired optical transparency for the thermoplastic film used in the present invention is between approximately 20 percent and 80 percent. In a desired embodiment of the present invention, the thermoplastic film has at least an approximately 80 percent optical transparency, and the thickness of the metal coating is such as to maintain an optical transparency greater than about 20 percent, so that diffraction patterns can be produced by either reflected or transmitted light. This corresponds to a metal coating thickness of about 5–40 nanometers (or ohms/square). However, in other embodiments of the invention, the metal thickness may vary significantly.

The preferred metal for deposition on the film is gold. However, silver, titanium, aluminum, chromium, copper, iron, zirconium, platinum, titanium, and nickel, as well as oxides of these metals, may be used. Chromium oxide can be used to make metalized layers.

The receptive material may be applied to the substrate by any one of a wide range of techniques. For example, the substrate surface may be coated with receptive material by application of solution in discrete arrays or patterns; spraying; ink jet; contact or other imprinting techniques; or printing a blocker material in a pattern followed by total immersion or spin coating with the receptive material. The technique selected should minimize the amount of receptive material required for coating a large number of test surfaces and maintain the stability/functionality of the receptive material during application. The technique should also apply or adhere the receptive material to the substrate in a uniform and reproducible fashion. Non-contact methods for applying the receptive material may be desired so as to eliminate the possibility of contamination by contact during application. Simple physisorption can occur on many materials, such as polystyrene, glass, nylon, polycarbonate, metals, or other materials well known to those skilled in the art. One particular embodiment of immobilizing the analyte-specific receptive material layer involves molecular attachment, such as that possible between thiol or disulfide-containing compounds and gold. Typically, a gold coating of about 5 to about 2000 nanometers thick is supported on a silicon wafer, glass, or polymer film (such as a MYLAR® film). The analyte-specific receptor attaches to the gold surface upon exposure of a solution of the receptive material, or through contact printing from a layer of receptive material on silicone stamp.

It is also contemplated that the receptive material layer may be formed on the substrate as a self-assembling monolayer of alkanethiolates, carboxylic acids, hydroxamic acids, and phosphonic acids on metalized thermoplastic films. The self-assembling monolayers have receptive material bound thereto. Reference is made to U.S. Pat. No. 5,922,550 for a more detailed description of such self-assembling monolayers and methods for producing the monolayers. The '550 patent is incorporated herein in its entirety for all purposes.

The present invention also contemplates applying the receptive material on the substrate member as a pattern of active analyte-specific regions in a photo-masking process as set forth in copending and commonly owned U.S. patent application Ser. Nos. 10/139,013; 10/139,025; 10/139,018; 10/138,598; 10/138,882; and 10/138,677 (incorporated herein by reference for all purposes). For example, a generally uniform coating or layer of receptive material may be applied to the entire substrate surface. A layer or coating of a blocking agent may be applied over the receptive material layer. A mask having any desired pattern of shielded areas and exposed areas (blank, transparent, or translucent areas) is then placed over the substrate member. The mask and substrate combination are then exposed to a particular stimulus (e.g., light) selected to activate the blocking agent under the exposed areas of the mask. The exposed areas thus define a pattern of inactive areas and the areas under the shielded areas of the mask define a pattern of active receptive material areas. After removal of the mask, the inactivated blocking agent is disassociated from the receptive material, for example in a subsequent rinsing or washing process.

In many instances, a "blocker" may be necessary to prevent non-specific binding. The term "blocker" as used herein means a reagent that adheres to the substrate surface so that it "blocks" or prevents non-analyte materials from binding to the surface (either in the patterned or un-patterned areas). The blocking step may be done as a post-treatment to a surface which has already-been coated with the receptive material ("post-block"). However, a "pre-block" technique may also be used wherein the substrate surface is pre-treated with a non-thiol containing blocker and then printed with the receptive material. It is believed that the printed material (usually sulfur containing) displaces the physisorbed blocker, thereby permitting the analyte-specific receptive material to be bound directly to the surface. A subsequent post-block may also be performed, if desired. Blockers can include, but are not limited to, proteins such as β-casein or albumins such as bovine serum albumin, pluronic or other surfactants, polyethylene glycol, polyvinyl alcohol, or sulfur derivatives of the above compounds, and any other blocking material known to those of ordinary skill in the art.

FIG. 1 is a schematic representation of a biosensor 10 and method of use of the biosensor for detecting and measuring an analyte of interest 20 according to the invention. In this example, the substrate 12 may be, for example, a β-casein pre-blocked gold Mylar film patterned with a thiolated antibody receptive material 14. The antibody 14 is specific for a particular analyte of interest, in this case the antigen 20, present in a test sample or medium. Antibody-coupled fluorescent beads 16 are added by one of the methods described above. The antibody 18 also has an affinity for the analyte of interest 20 and attaches to a different epitope of the analyte 20, as described above. If the analyte 20 is present in the medium, an immune complex is formed as depicted in the figure. Upon subsequent exposure of the substrate with attached complex to a light source 22, an optical diffraction pattern 26 is generated corresponding to the pattern of the thiolated antibody 14 on the substrate. The beads 16 may enhance or cause the diffraction, particularly if the analyte of interest 20 is not of a size that results in a diffraction pattern without diffraction enhancing elements. The light source 22 also results in a detectable and measurable amount of fluorescence 24 that may be measured by an appropriate instrument, such as a fluoroscope or fluorometer.

The biosensors according to the invention have a wide range of uses in any number of fields. The uses for the biosensors of the present invention include, but are not limited to, detection of chemical or biological contamination in garments, such as diapers, generally the detection of contamination by microorganisms in prepacked foods such as meats, fruit juices or other beverages, and the use of the biosensors of the present invention in health diagnostic applications such as diagnostic kits for the detection of proteins, hormones, antigens, nucleic acids, DNA, microorganisms, and blood constituents. The present invention can also be used on contact lenses, eyeglasses, window panes, pharmaceutical vials, solvent containers, water bottles, band-aids, wipes, and the like to detect contamination. In one embodiment, the present invention is contemplated in a dipstick form in which the patterned substrate is mounted at the end of the dipstick. In use the dipstick is dipped into the liquid in which the suspected analyte may be present and allowed to remain for several minutes. The dipstick is then removed and then, either a light is projected through the substrate or the substrate is observed with a light reflected from the substrate. If a diffraction pattern is observed, then the analyte is present in the liquid.

In another embodiment of the present invention, a multiple analyte test is constructed on the same support. A strip may be provided with several patterned substrate sections. Each section has a different receptive material that is different for different analytes. It can be seen that the present invention can be formatted in any array with a variety of patterned substrates thereby allowing the user of the biosensor device of the present invention to detect the presence of multiple analytes in a medium using a single test.

In yet another embodiment of the present invention, the biosensor can be attached to an adhesively backed sticker or decal which can then be placed on a hard surface or container wall. The biosensor can be placed on the inside surface of a container such as a food package or a glass vial. The biosensor can then be visualized to determine whether there is microbial contamination.

The invention is further illustrated by the following examples, which are not to be construed in any way as imposing limitations upon the scope of the invention. It should be understood that resort may be had to various other embodiments, modifications, and equivalents thereof, which, after reading the description of the invention herein, may suggest themselves to those skilled in the art without departing from the scope and spirit of the present invention.

EXAMPLES

An example of derivation of an antibody to C-reactive protein (CRP) or Luteinizing hormone (LH) follows: To 1 mg of antibody was added 450 μl phosphate buffered saline (PBS) and 50 μl of 10 mM aqueous solution of sulfo-LC-SPDP (Pierce Catalog# 21650). After 60 minutes at room temperature, the solution is desalted in a D-Salt™ polyacrylamide desalting column (Pierce Catalog # 43240ZZ). An acetate buffer, pH4.5 is used if a subsequent reduction of the disulfide bond is to be done, while a PBS buffer, pH7.5, is used if the antibody derivative is to remain as the disulfide. 500 μl fractions were collected from the column, and the fractions with antibody derivative was determined using a Coomassie® plus protein Assay.

The resulting thiolated antibody, either disulfide or thiol, may be contact printed on gold-coated MYLAR®. For example, an elastomeric stamp with raised features in a desired pattern is soaked in a 0.5 mg/ml concentration of the thiolated antibody for 10 minutes, followed by drying the stamp under nitrogen gas or air stream, and then contacted with a gold-coated MYLAR® film for 10–120 seconds.

Antibody-conjugated polystyrene fluorescent-labeled particles were produced by carbodiimide coupling with ethyldimethylaminodicarbodiimide (EDAC, bottle#3 of polysciences kit, Catalog#19539). For example, 0.125 ml of a 10% suspension of 0.5 micron diameter carboxylated fluorescent-labeled particles (Molecular probes, Catalog # F-8812) were activated with an aqueous solution of the EDAC for 1–4 hours, rinsed, and then exposed to 300 micrograms of a monoclonal antibody to LH or CRP. The particles were blocked with ethanolamine (0.5–5 M) or bovine serum albumin (0.01–10 mg/ml) for un-reacted activated groups, and then rinsed with PBS buffer. Finally, the particles were stored in PBS buffer at 4° C. with constant rotation.

Figure 2:
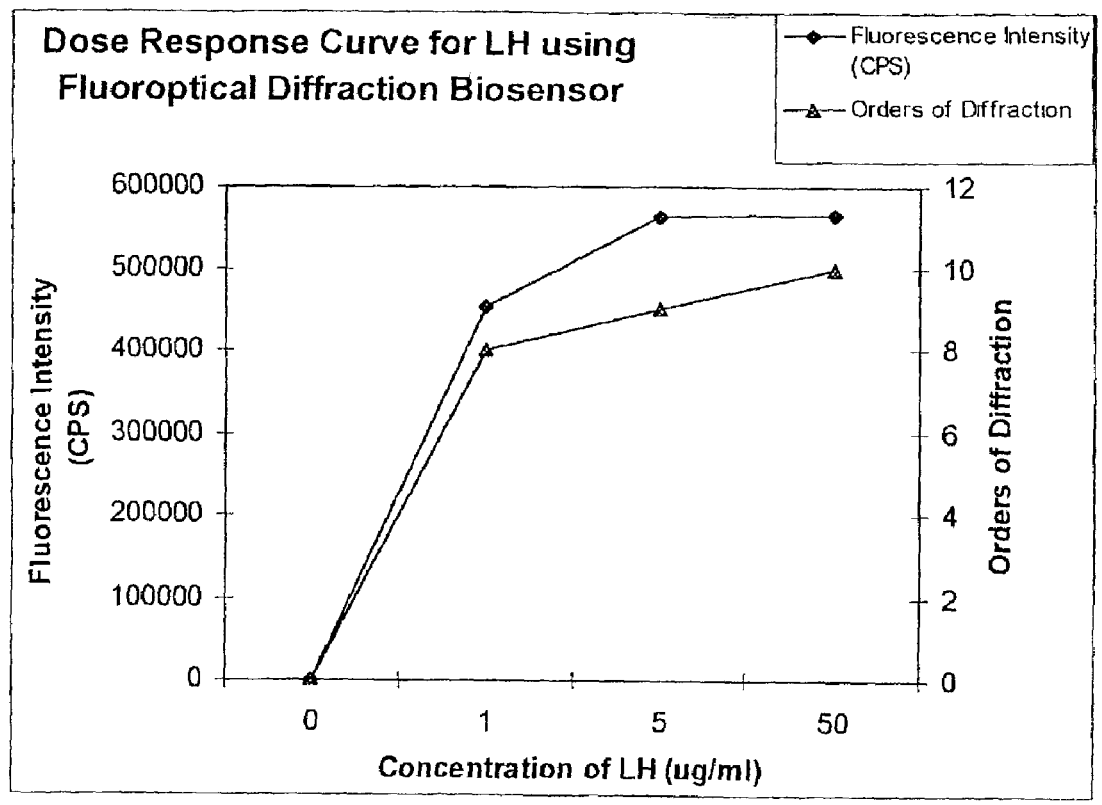
FIG. 2 is a dose response curve for Luteinizing Hormone (LH) generated from a biosensor according to the present invention.

In forming an embodiment of a diffraction based fluorescent biosensor according to the invention as a sandwich immunoassay system, first the thiolated LH MAb#1 (antibody raised for LH β-subunit) is contact printed on a β-casein pre-blocked gold Mylar film which allows the antibody to be placed in an organized pattern on a surface. The LH antigen standards, controls and unknown samples are added to each biosensor and allowed to interact with LH MAb#1 antibody for about 5 minutes. Then, the fluorescent-labeled LH MAb#2 (antibody raised for LH α-subunit) coupled beads are added to form a sandwich type immune complex for 10 minutes. Excess reagents are wicked away with a membrane filter (e.g., diameter 1.6 mm). Each biosensor is analyzed for optical diffraction and fluorescence. As shown in the FIG. 2, the results (orders of diffraction and fluorescence intensity) may be represented in a dose response curve for Luteinizing Hormone (LH). A high order of diffraction signifies that the analyte (LH) is present, and the fluorescence intensity is a quantitative measurement of the amount of the analyte.

Figure 3:
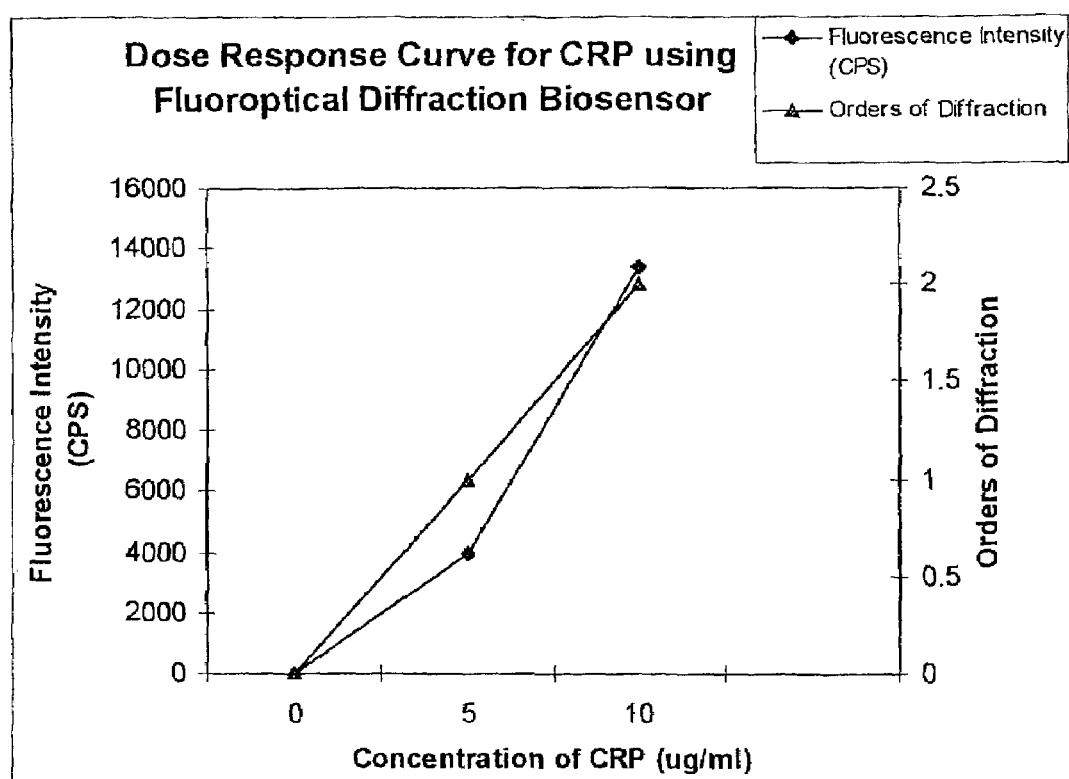
FIG. 3 is a dose response curve for C-reactive protein (CRP) generated from a biosensor according to the present invention.

As shown in FIG. 3, a dose response curve for CRP was produced as follows: First, the thiolated CRP MAb#1 antibody is printed on a β-casein pre-blocked gold Mylar film which allows the antibody to be placed in an organized pattern on a surface. The CRP antigen standards, controls and unknown samples are added to each biosensor and allowed to interact with CRP MAb#1 antibody for 5 minutes. Then, the fluorescent-labeled CRP MAb#2 antibody coupled beads are added to form a sandwich type immune complex. Excess reagents are wicked away with a membrane filter (e.g., 1.6 mm diameter). Each biosensor is analyzed for optical diffraction and fluorescence.

It should be understood that resort may be had to various other embodiments, modifications, and equivalents to the embodiments of the invention described herein which, after reading the description of the invention herein, may suggest themselves to those skilled in the art without departing from the scope and spirit of the present invention.

What is claimed is:

1. A method of detecting an analyte of interest in a medium with a diffraction based biosensor having at least one additional detection tag mechanism, comprising:
    exposing a detection tag material to the medium, the detection tag material tagging the analyte of interest with a measurable parameter in addition to optical diffraction characteristics of the analyte of interest;
    exposing a biosensor to the medium, the biosensor having a substrate member with a receptive material layer applied to at least one side thereof wherein the receptive material is specific for the analyte of interest such that the analyte binds to the receptive material;
    separating an unbound detection tag material from a bound detection tag material tagging the analyte of interest;
    exposing the biosensor to a light source and detecting the presence of the analyte by detecting a diffraction pattern of the transmitted light or reflected light; and
    detecting the emitted measurable parameter of the detection tag material.

2. The method as in claim 1, wherein the detection tag material is a fluorescence emitting substance.

3. The method as in claim 2, wherein the amount of fluorescence emitted by the substance is quantitatively measured.

4. The method as in claim 2, wherein the fluorescence emitting substance is fluorescent-labeled diffraction enhancing elements having a receptor material specific for the analyte of interest such that the elements bind to the analyte of interest in the medium.

5. The method as in claim 4, wherein the fluorescent-labeled diffraction enhancing elements are beads.

6. The method as in claim 2, wherein the fluorescence emitting substance is a fluorescent dye or tracer that stains the analyte of interest in the medium.

7. The method as in claim 1, wherein the detection tag material is one of a color-based, radiation-based, and chemical induced luminescence-based substance.

8. The method as in claim 1, wherein the detection tag material is added to the medium prior to exposing the biosensor to the medium.

9. The method as in claim 8, wherein the detection tag material is fluorescent-labeled diffraction enhancing elements that bind to the analyte of interest in the medium.

10. The method as in claim 1, wherein the detection tag material is added to the medium after exposing the biosensor to the medium.

11. The method as in claim 10, wherein the detection tag material is fluorescent-labeled diffraction enhancing elements that bind to the analyte of interest after the analyte has bound to the receptive material on the substrate.

12. The method as in claim 1, wherein the detection tag material is added to the medium simultaneously with exposing the biosensor to the medium.

13. The method as in claim 12, wherein the detection tag material is fluorescent-labeled diffraction enhancing elements that bind to the analyte of interest in the medium and the analytes which have already been bound to the receptive material on the substrate.

14. The method as in claim 1, comprising selecting the substrate member from the group of materials consisting of plastics, metal coated plastics and glass, functionalized plastics and glass, silicon wafers, metal oxides, glass, and foils.

15. The method as in claim 14 wherein the substrate member comprises a polymer film coated with a metal.

16. The method as in claim 15, wherein the polymer film comprises polyethylene-terephthalate.

17. The method as in claim 15, comprising selecting the metal from the group consisting of gold, silver, chromium, nickel, platinum, aluminum, iron, copper, gold oxide, titanium, chromium oxide, silver oxide, and zirconium.

18. The method as in claim 1, comprising viewing the diffraction pattern with the naked eye or a viewing device.

19. The method as in claim 1, comprising selecting the receptive material from at least one of antigens, antibodies, nucleotides, chelators, enzymes, bacteria, yeasts, fungi, viruses, bacterial pili, bacterial flagellar materials, nucleic acids, polysaccharides, lipids, proteins, carbohydrates, metals, hormones, peptides, aptamers, and respective receptors for said materials.

20. The method as in claim 1, wherein the analyte of interest is selected from at least one of a bacteria, yeast, fungus, virus, rheumatoid factor, IgG, IgM, IgA, IgD, and IgE antibodies, carcinoembryonic antigen, *streptococcus* Group A antigen, viral antigens, antigens associated with autoimmune disease, allergens, tumor antigens, streptococcus group B antigen, HIV I or HIV II antigen, antibodies viruses, antigens specific to RSV, an antibody, antigen, enzyme, hormone, polysaccharide, protein, lipid, carbohydrate, drug, nucleic acid, *Neisseria meningitides* groups A, B, C, Y and W sub 135, *Streptococcus pneumoniae, E. coli* K1, *Haemophilus influenza* type A/B, an antigen derived from microorganisms, PSA and CRP antigens, a hapten, a drug of abuse, a therapeutic drug, environmental agents, or antigens specific to Hepatitis.

21. The method as in claim 1, wherein the receptive material is printed in a pattern on the substrate member, and further comprising applying a blocking material to non-printed areas of the substrate member.

* * * * *

UNITED STATES PATENT AND TRADEMARK OFFICE
CERTIFICATE OF CORRECTION

PATENT NO. : 7,091,049 B2 Page 1 of 1
APPLICATION NO. : 10/180219
DATED : August 15, 2006
INVENTOR(S) : Boga et al.

It is certified that error appears in the above-identified patent and that said Letters Patent is hereby corrected as shown below:

On Title Page item 56
Column 2, line 2, delete "10/139,02," and insert --10/139,025,--

Signed and Sealed this

Second Day of January, 2007

JON W. DUDAS
*Director of the United States Patent and Trademark Office*